United States Patent [19]
Mallinson et al.

[11] Patent Number: 6,111,154
[45] Date of Patent: *Aug. 29, 2000

[54] HIGH ENERGY DENSITY STORAGE OF METHANE IN LIGHT HYDROCARBON SOLUTIONS

[75] Inventors: Richard G. Mallinson; Kenneth E. Starling; Jeffrey H. Harwell, all of Norman, Okla.

[73] Assignee: The Board of Regents of The University of Oklahoma, Norman, Okla.

[ * ] Notice: This patent is subject to a terminal disclaimer.

[21] Appl. No.: 09/305,177

[22] Filed: May 4, 1999

Related U.S. Application Data

[63] Continuation of application No. 08/699,765, Aug. 20, 1996, Pat. No. 5,900,515.

[51] Int. Cl.$^7$ .................................................... C10L 3/00
[52] U.S. Cl. .................................. 585/6; 585/14; 48/127.3
[58] Field of Search ........................... 585/6, 14; 48/127.3

[56] References Cited

U.S. PATENT DOCUMENTS

| | | | |
|---|---|---|---|
| 3,760,597 | 9/1973 | Becker | 62/47 |
| 5,315,054 | 5/1994 | Teel | 585/14 |
| 5,900,515 | 5/1999 | Mallinson et al. | 585/6 |

*Primary Examiner*—Walter D. Griffin
*Assistant Examiner*—Nadine Preisch
*Attorney, Agent, or Firm*—Dunlap, Codding & Rogers, P.C.

[57] ABSTRACT

Method for storing methane in light hydrocarbons at moderate temperatures and pressures such that the resulting solution has a high energy density. The method includes combining methane at a 50 to 80 mole percent concentration with a light hydrocarbon, such as butane, propane or liquid petroleum gas (LPG). Then the resulting solution is maintained at a temperature of between $-1°$ C. and $38°$ C. and a pressure of between 8 and 14 MPa. Under these parameters, the solution has an energy density which is 40 to 67 percent that of gasoline. A motor vehicle fuel storage apparatus for the method includes an insulated storage tank containing the 50 to 80 mole percent methane solution and a cooling mechanism for maintaining the methane solution between $-1°$ C. and $38°$ C. The cooling mechanism may be an arrangement of expansion valves, or connection to the air conditioning system of the vehicle, or both.

9 Claims, 14 Drawing Sheets

BUBBLE CURVES FOR THE METHANE AND N-BUTANE SOLUTIONS.

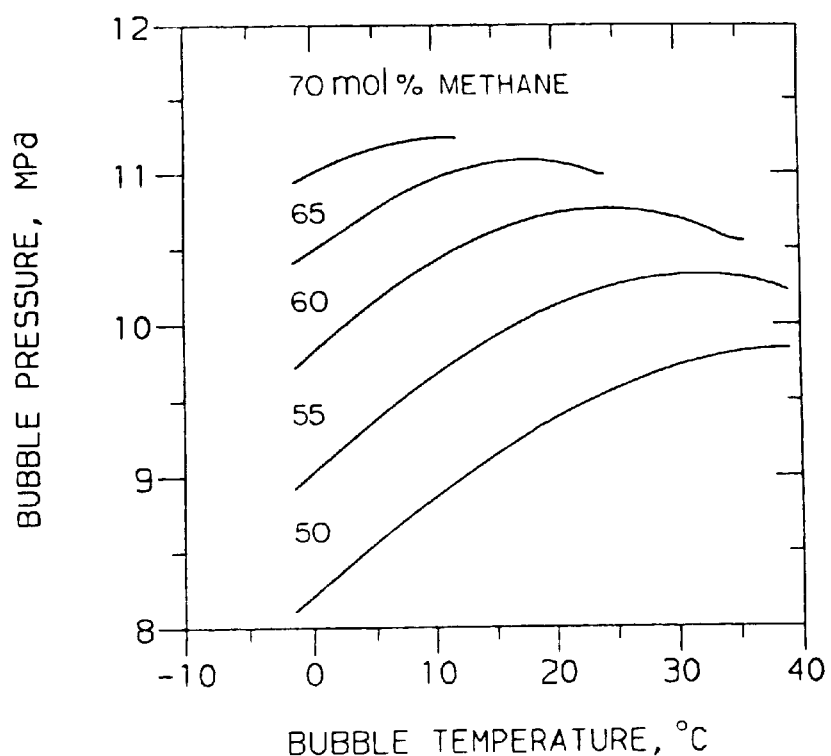
BUBBLE CURVES FOR THE METHANE AND PROPANE SOLUTIONS.
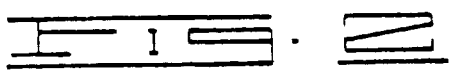

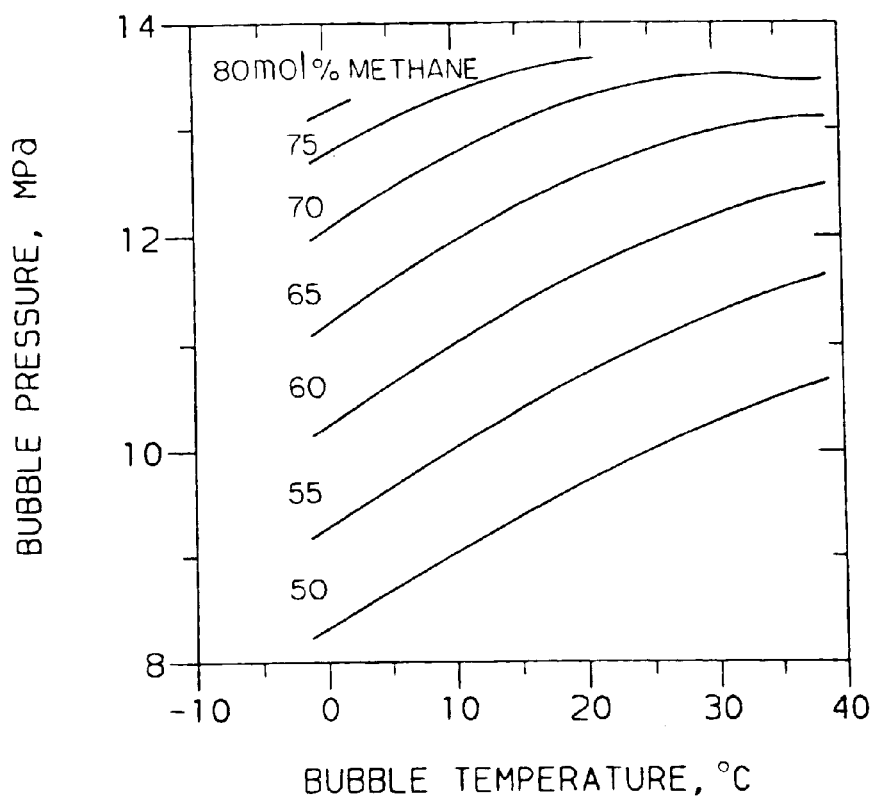
BUBBLE CURVES FOR THE METHANE AND LPG SOLUTIONS.
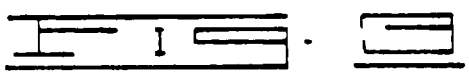

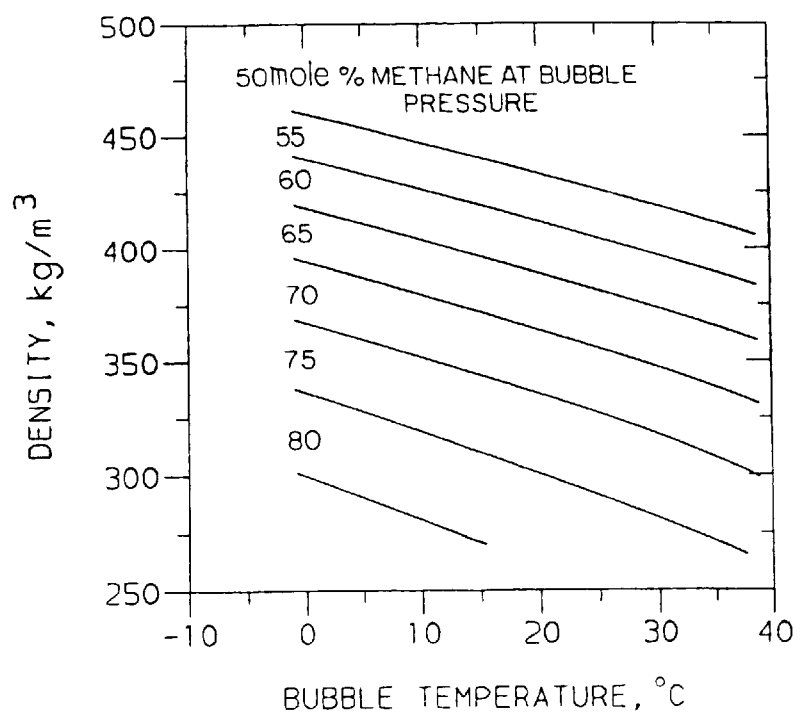
DENSITY CURVES FOR THE METHANE AND N-BUTANE SOLUTIONS.
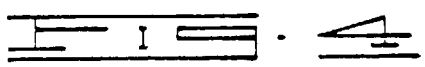

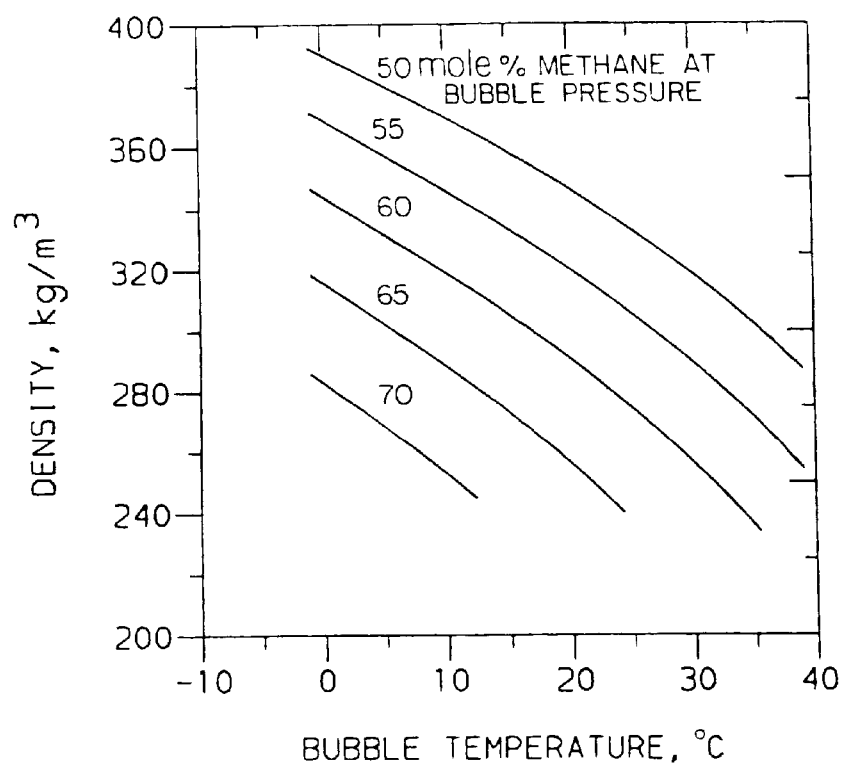
DENSITY CURVES FOR THE METHANE AND PROPANE SOLUTIONS.
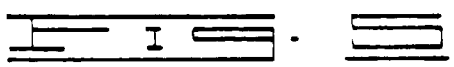

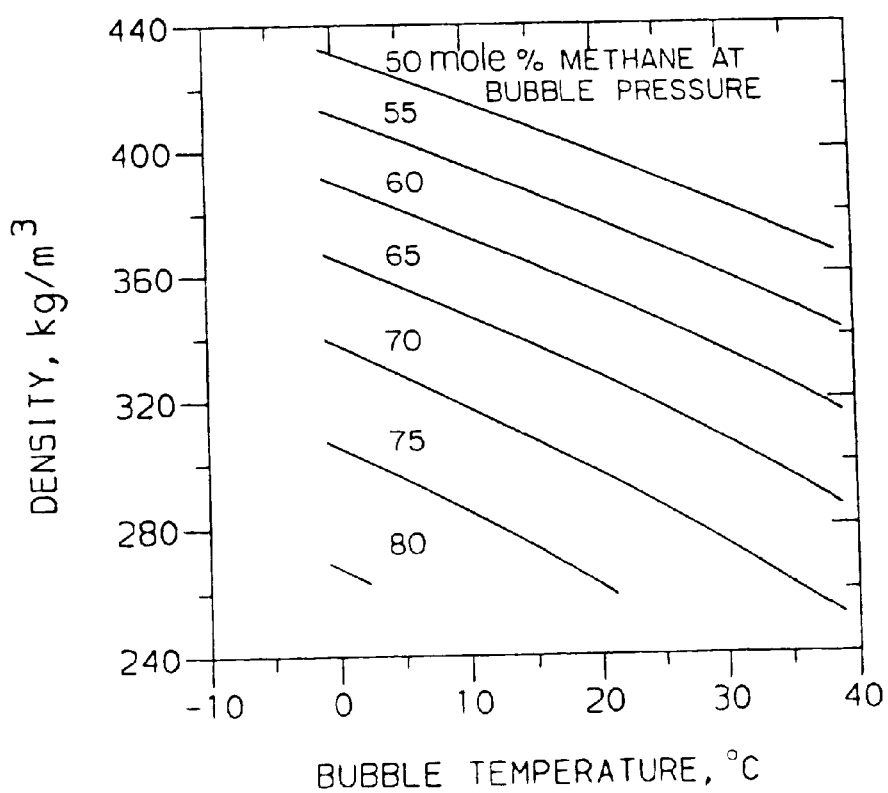
DENSITY CURVES FOR THE METHANE AND LPG SOLUTIONS.
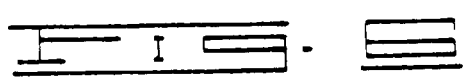

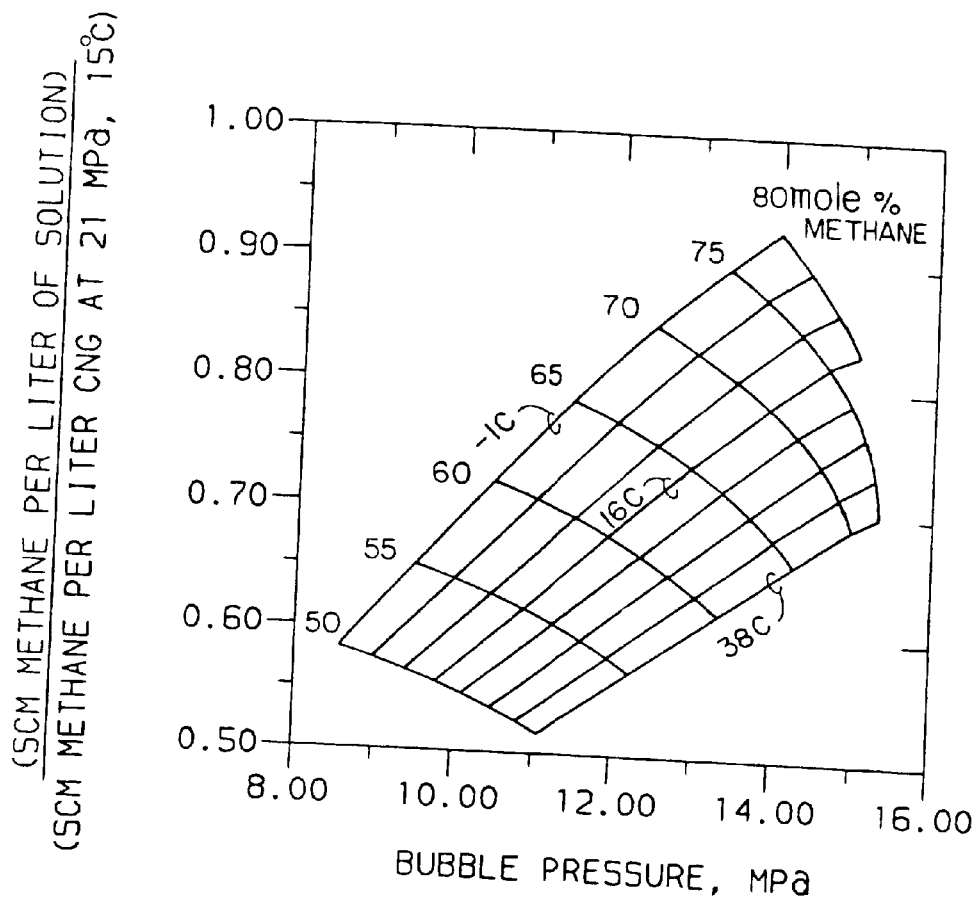
COMPARISON OF THE AMOUNT OF METHANE STORED IN N-BUTANE TO THE AMOUNT OF METHANE IN CNG AT 21 MPa.
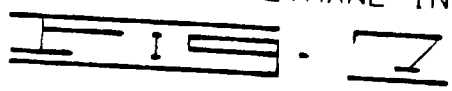

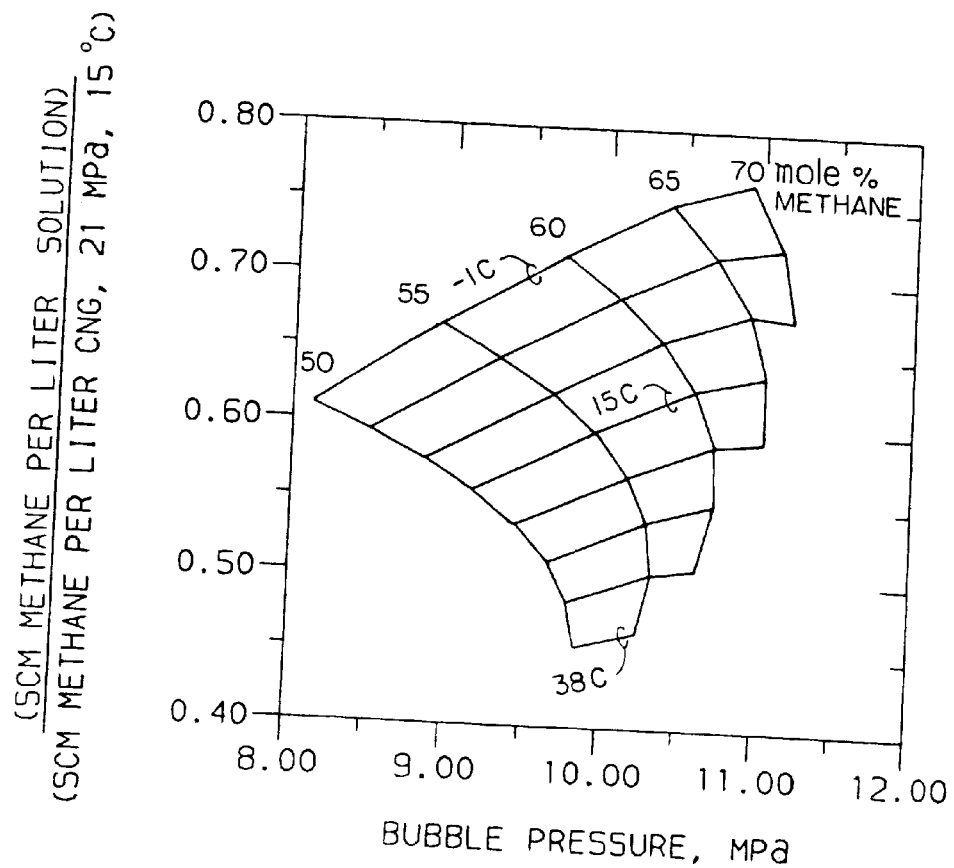
COMPARISON OF THE AMOUNT OF METHANE STORED IN PROPANE TO THE AMOUNT OF METHANE IN CNG AT 21 MPa.
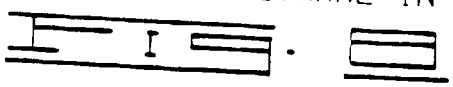

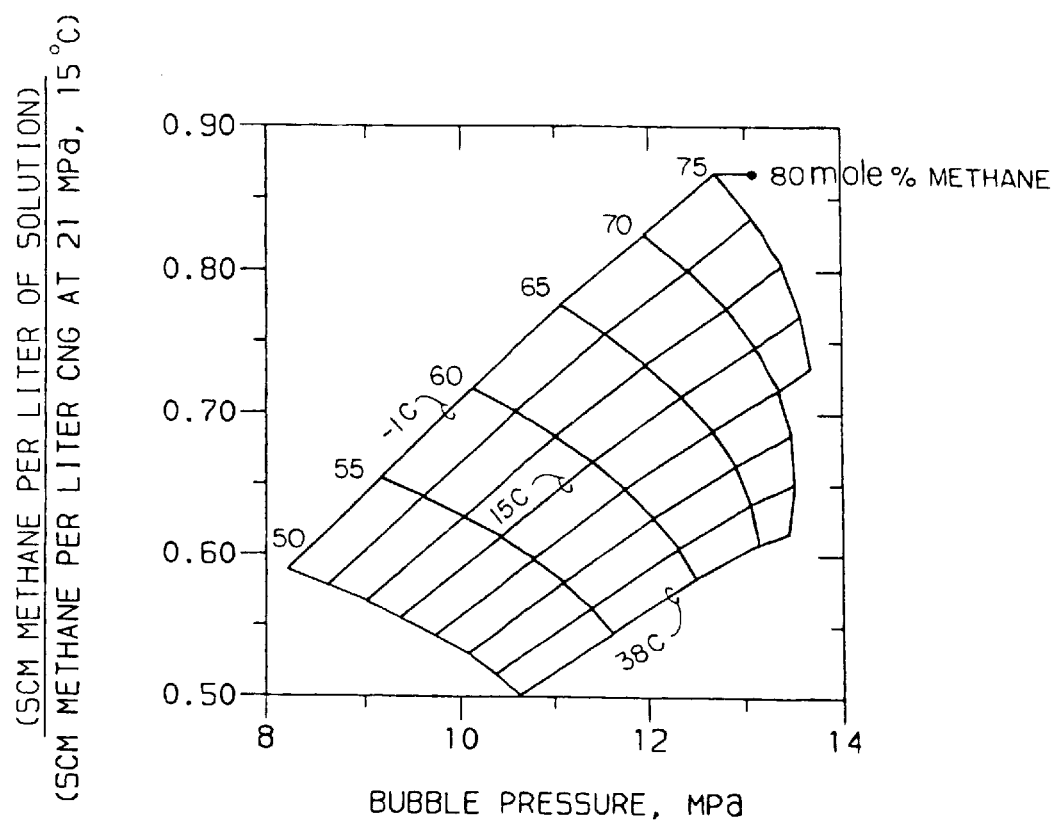
COMPARISON OF THE AMOUNT OF METHANE STORED IN LPG TO THE AMOUNT OF METHANE IN CNG AT 21 MPa.
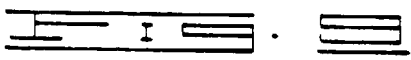

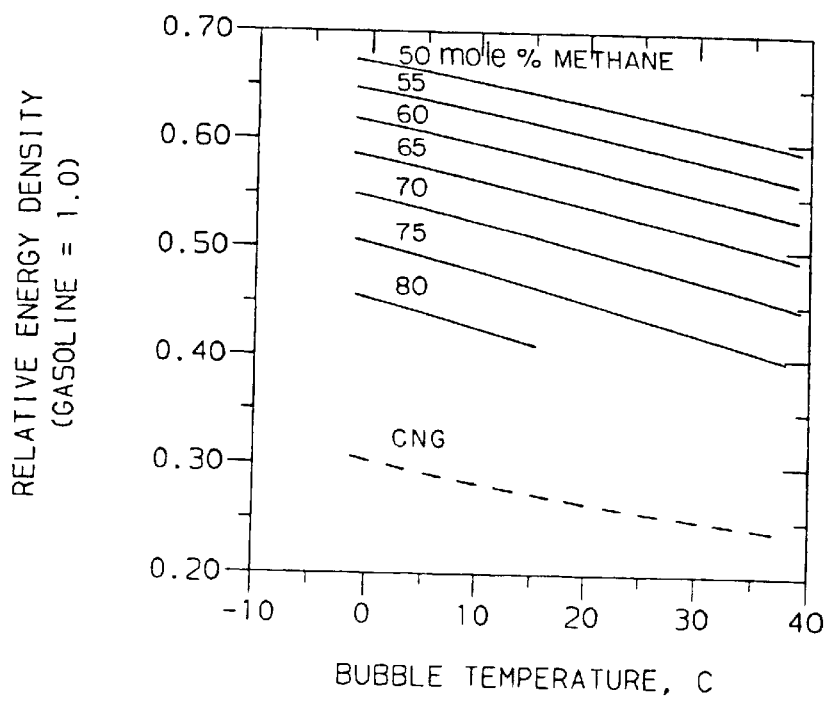
ENERGY DENSITY CURVES FOR THE METHANE IN N-BUTANE SOLUTIONS.
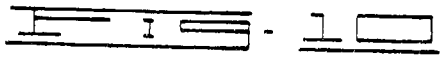

ENGERGY DENSITY CURVES FOR THE METHANE IN PROPANE SOLUTIONS.

ENGERGY DENSITY CURVES FOR THE METHANE IN LPG SOLUTIONS.

HIGH ENERGY DENSITY STORAGE OF METHANE IN LIGHT HYDROCARBON SOLUTIONS

This application is a continuation of U.S. Ser. No. 08/699,765, filed Aug. 20, 1996, now U.S. Pat. No. 5,900,515.

BACKGROUND OF THE INVENTION

1. Field of the Invention

The present invention relates generally to liquid fuel solutions of hydrocarbons and particularly to the storage of natural gas, primarily for vehicular use, in liquid solution with other hydrocarbons.

2. Description of Related Art

Composed essentially of methane, natural gas (NG) is an important competitor in the field of alternative fuels. NG is economic, and it offers a greater reduction in CO, $NO_x$ and non-methane hydrocarbon (NMHC) emissions. However, the on-board storage limitations of NG are a severe drawback to the use of NG as a vehicular fuel.

Conventional storage techniques for NG involve compression and liquefaction methods. The former is termed compressed natural gas (CNG) while the latter is known as liquefied natural gas (LNG). CNG requires bulky, high-pressure vessels to store a quantity of NG that delivers about one-sixth the range of an equal amount of gasoline under normal operating conditions. LNG provides nearly two-thirds the range of a comparable volume of gasoline, but requires cryogenic processing equipment and cryogenic storage.

In addition to the on-board storage problems of CNG and LNG, the logistics of the preparation and delivery of these fuels pose inconveniences. CNG at 21 MPa requires a delivery system operating above the storage pressure to ensure that a full charge is obtained. Therefore, a compression plant must be at or very near the vehicle refueling site.

LNG is liquified through a cryogenic procedure, and then delivered to a staging area before being dispensed to vehicles. This method requires a heavily insulated storage vessel to stage the fuel and a similarly insulated tank on board the vehicle.

In view of the drawbacks associated with CNG and LNG storage techniques, it is highly desirable to devise a safe, economical and convenient way to store NG for use as a vehicular fuel. A practical natural gas storage system should be characterized by (1) moderate storage pressures, so that high-pressure vessels like those required for storage of CNG are unnecessary; and (2) moderate storage temperatures, so that cryogenic equipment needed for storage of LNG is not a requirement.

SUMMARY OF THE INVENTION

The present invention is a method for storing natural gas at moderate temperatures and pressures in solutions having high energy densities. The method includes providing a storage tank, introducing a mixture of methane and at least one other light hydrocarbon into the storage tank, and maintaining the mixture at moderate temperatures and pressures such that the mixture has an energy density greater than about 11,000 $MJ/m^3$.

For vehicular use, an apparatus constructed in accordance with the present invention includes a vehicular storage tank containing a fuel mixture of methane and at least one other light hydrocarbon. Optionally, a cooling system to maintain the fuel mixture at a sub-ambient temperature may be provided.

One object of the present invention is to provide a mixture of methane and at least one other light hydrocarbon at a moderate temperature and pressure such that the mixture has an energy density greater than compressed natural gas (CNG) at a pressure of 24.2 MPa.

A second object of the present invention is to provide a mixture of methane and at least one other light hydrocarbon at a moderate temperature and pressure such that the mixture has an energy density in the range of propane at 1.4 MPa, i.e in the range of 23,500 $MJ/m^3$.

A third object of the present invention is to provide a vehicle storage tank which can be filled with a mixture of methane and at least one other light hydrocarbon at a moderate temperature and pressure from conventional fueling stations.

A fourth object of the present invention is to provide a vehicle storage tank which is capable of maintaining a mixture of methane and at least one other light hydrocarbon at a moderate temperature and pressure at ambient air temperatures of about 38° C. as the mixture is depleted from the vehicle storage tank.

A fifth object of the present invention is to provide a high energy density fuel mixture for pipeline transmission. By providing a high energy density fuel mixture, the pipeline pressure can be decreased without reducing the amount of energy being sent through the pipeline. Alternatively, the same pipeline pressure may be used to send a greater amount of energy through the pipeline because of the high energy density of the fuel mixture.

A sixth object of the present invention is to provide a high energy density fuel mixture for use in electric generating stations, emergency generators or back-up generators. Some electric power plants use fuel oil as a back-up or alternate fuel. Because of heating requirements in the winter, fuel oil may be expensive and in short supply. The present invention provides storage of a high energy density methane fuel mixture which may be used as an alternate fuel for electric generating units. Moreover, cold ambient temperatures allow increased volumes of methane in the fuel mixture to achieve even higher energy densities. Thus, the methane mixtures disclosed herein may be substituted for any application employing fuel oil or the like and methane mixtures burn more cleanly than fuel oil.

Other objects, features and advantages of the present invention are apparent from the following detailed description when read in conjunction with the accompanying drawings and appended claims.

BRIEF DESCRIPTION OF THE DRAWINGS

FIG. 2 is a graph of bubble pressure versus bubble temperature for methane and propane solutions between 50 mole percent methane and 70 mole percent methane.

FIG. 3 is a graph of bubble pressure versus bubble temperature for methane and LPG solutions between 50 mole percent methane and 80 mole percent methane.

FIG. 4 is a graph of density versus bubble temperature for methane and n-butane solutions between 50 mole percent and 80 mole percent methane.

FIG. 5 is a graph of density versus bubble temperature for methane and propane solutions between 50 mole percent and 70 mole percent methane.

FIG. 6 is a graph of density versus bubble temperature for methane and LPG solutions between 50 mole percent and 80 mole percent methane.

FIG. 7 is a graphical comparison of the amount of methane stored in n-butane with the amount of methane stored in CNG (21 MPa). The methane/n-butane solutions are between 50 mole methane and 80 mole methane in a range of temperatures and bubble pressures.

FIG. 8 is a graphical comparison of the amount of methane stored in propane with the amount of methane stored in CNG (21 MPa). The methane/propane solutions are between 50 mole methane and 70 mole methane in a range of temperatures and bubble pressures.

FIG. 9 is a graphical comparison of the amount of methane stored in LPG with the amount of methane stored in CNG (21 MPa). The methane/LPG solutions are between 50 mole methane and 80 mole methane in a range of temperatures and bubble pressures.

FIG. 10 is a graph of energy density versus bubble temperature for methane in n-butane solutions between 50 mole percent methane and 80 mole percent methane.

DETAILED DESCRIPTION OF THE PREFERRED EMBODIMENTS

Figure 1:
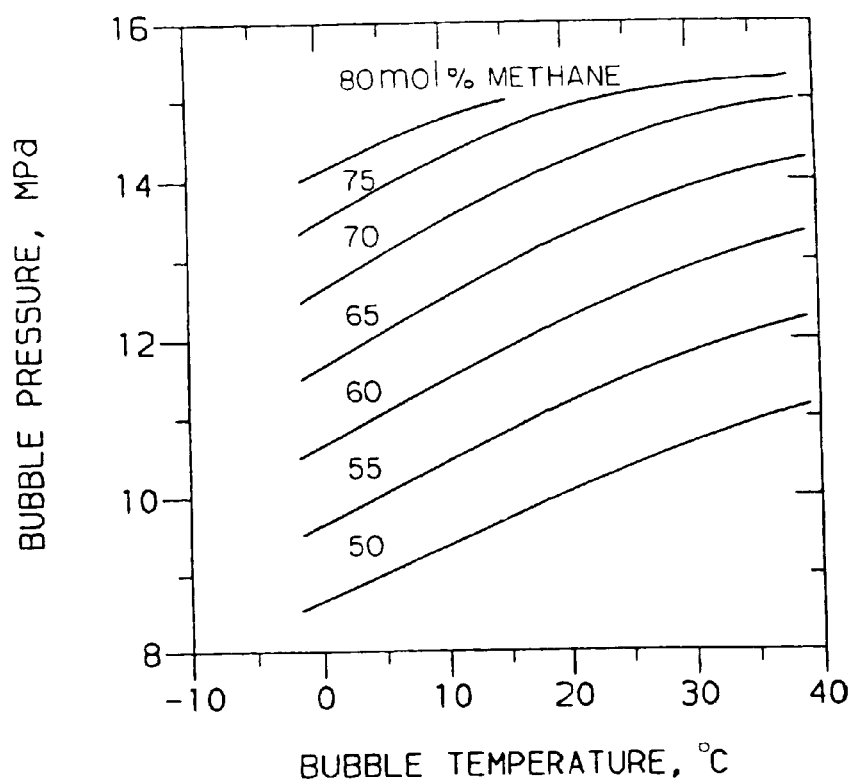
FIG. 1 is a graph of bubble pressure versus bubble temperature for methane and n-butane solutions between 50 mole percent methane and 80 mole percent methane.

Quantification of mixture properties such as density, enthalpy, entropy, heat capacities, etc. are usually not readily obtained from tabulated data, but must be determined by calculation. The assumption of an ideal solution allows one to calculate the properties of a mixture as the summation of the individual components in solution. However, the properties of a real solution are not necessarily ideal because, upon mixing, the individual components of real solutions may undergo additional interaction characteristics which affect fluid properties. Nevertheless, solution properties can be estimated through the use of an equation of state that accounts for the solution's deviation from the ideal.

The equation of state used herein for solutions of methane in light hydrocarbons is the Benedict-Webb-Rubin-Starling (BWRS) equation, show below. In this equation, the pressure P is a function of the temperature T and the molar density r. The other terms ($A_0$, $B_0$, $C_0$, $D_0$, $E_0$, a, b, c, d, a, g) are mixture parameters for the specific interactions of the components in the mixture of interest.

$$P = RT\rho + \left[B_0 RT - A_0 - \frac{C_0}{T^2} + \frac{D_0}{T^3} - \frac{E_0}{T^4}\right]\rho^2 +$$

$$\left[bRT - a - \frac{d}{T}\rho^3 + \alpha\left[a + \frac{d}{T}\rho^6 + c\frac{\rho^2}{T^2}[1 + \gamma\rho^2]\exp[-\gamma\rho^2]\right]\right]$$

This equation is very good for gases and light hydrocarbons because it accounts for binary interactions of these types of compounds very well. The usefulness of this equation is that it extends into both liquid and vapor phase calculations with very good accuracy. Thus, the properties of solutions in either the gaseous or liquid state can be determined based on the temperature and pressure conditions.

The utility of the BWRS equation in vapor liquid equilibrium calculations is in predicting the bubble conditions of solutions. These conditions are the temperature and pressure at which a mixture of a specific composition is saturated, i.e. the liquid is on the verge of vaporizing.

The determination of the bubble point for solutions of NG in other hydrocarbons yields insight into the maximum amount of NG (as a function of the mole fraction of methane) that can be stored in liquid phase at a given temperature and pressure.

The solvents used for this analysis were n-butane, propane and an arbitrary LPG mixture, which is shown below:

| Component | Mole Percent |
| --- | --- |
| Ethane | 0.02 |
| Propane | 36.23 |
| Isobutane | 33.63 |
| n-Butane | 29.58 |
| Isopentane | 0.46 |
| n-Pentane | 0.08 |

Heavier components such as $C_6$ and above were excluded from the analysis. While high mole fractions of methane are obtainable in the heavier hydrocarbons, the relative volume of methane which can be stored is far less than in the lighter hydrocarbons. Additionally, n-butane, isobutane, propane and liquid petroleum gas (LPG) are solvents which are readily available for commercial use.

It should be appreciated that mixtures may include small amounts of ethane or higher hydrocarbons without departing from the scope and purpose of the present invention. Further, butane in the form of n-(normal) or I-(iso) may be a constituent of fuel mixtures contemplated by the present invention and frequently amounts of both n-butane and isobutane are at least trace components of such mixtures.

Vapor liquid equilibrium calculations may be performed for solutions of methane with these three solvents over a range of temperatures and mole fractions of methane. Solutions with mole fractions of methane less than 50 percent exhibit properties more like the solvent. Therefore, solutions with mole fractions of methane between 50 and 80 percent are most relevant to the present invention. However, it should be appreciated that higher methane content is possible, but at the cost of having to achieve and maintain lower temperatures.

The temperature range of interest is that which represents normal conditions. Thus, the upper end of relevant temperature range is the temperature that can be maintained on a hot day. An arbitrary temperature of 38° C. was chosen for the upper end of the temperature range.

The lower end of the temperature range represents a low temperature which can be achieved without cryogenic cooling. For purposes of analysis, -1° C. was selected as the lower end of the temperature range. This low temperature allows the avoidance of special materials for tanks and pipes and permits the use of normal cooling equipment which employs freon or freon substitutes as refrigerants.

FIGS. 1 through 3 show the bubble conditions of various mole fractions of methane in butane, propane and LPG. The bubble pressures of all the solutions are seen to increase with a corresponding increase in the mole percentage of methane.

As the mole fraction of methane is increased, the vapor pressure of the solution increases. Therefore, a higher pressure is required to offset the higher vapor pressure of the solution.

Solution Energy Densities

Table A below presents a summary of the energy densities of a number of pure hydrocarbon liquids and gases. Because hydrocarbon mixtures having high propane content are used extensively for vehicle transportation fuels, it is interesting to compare the conditions at which the energy densities of these pure hydrocarbons equal or exceed the energy density of propane.

Because natural gas is principally methane, the gross heating value 9,474 MJ/m$^3$ of methane at 38° C. and 24 MPa is representative of compressed natural gas (CNG) vehicle fuel. A drawback to the use of CNG as a vehicle fuel is this relatively low energy density compare to gasoline, which generally has an energy density of 31,600 to 37,200 MJ/m$^3$, depending on the gasoline composition. Thus, the energy density of CNG at 24 MPa generally is less than 30% of gasoline energy densities.

TABLE A

Energy Densities of Pure Hydrocarbon Fluids

| Fuel | Phase | Temp ° C. | Pressure MPa | Gross Heating Value, MJ/m$^3$ |
| --- | --- | --- | --- | --- |
| methane | liquid | −162 | 0.1 | 23,574 |
| ethane | liquid | −73 | 0.1 | 23,577 |
| propane | liquid | 38 | 1.4 | 23,580 |
| isobutane | liquid | 38 | 0.5 | 26,313 |
| n-butane | liquid | 38 | 0.5 | 27,492 |
| isopentane | liquid | 38 | 0.2 | 29,216 |
| n-pentane | liquid | 38 | 0.2 | 29,371 |
| n-hexane | liquid | 38 | 0.1 | 31,174 |
| n-heptane | liquid | 38 | 0.1 | 32,052 |
| n-octane | liquid | 38 | 0.1 | 32,891 |
| methane | gas | 38 | 0.1 | 38 |
| methane | gas | 38 | 24 | 9,474 |
| methane | gas | 38 | 259 | 23,580 |
| ethane | gas | 38 | 0.1 | 66 |
| ethane | gas | 38 | 46 | 23,580 |

Commercial propane mixtures, which are principally propane, have been used as vehicle fuels because net energy costs are lower than gasoline. The energy densities of commercial propane mixtures are generally 65–75% of the energy densities of gasolines, so that with 35% larger fuel tanks the propane fuel vehicle range is the same as for gasoline fuel.

It should be apparent from the above background information that it is desirable to improve the energy density of natural gas beyond the energy density of CNG at 24 MPa, i.e. beyond 9,474 MJ/m$^3$. It is even more desirable to improve the energy density of natural gas into the range of propane energy densities, i.e. into the range of 23,580 MJ/m$^3$.

With reference to FIGS. 4 through 6, shown therein is the density of each solution plotted against the bubble temperature with the different mole percentages of methane as a parameter. It should be noted that these mixtures are also at the bubble pressure corresponding to the individual mixture-temperature and composition conditions.

From inspection of FIGS. 4 through 6, it is apparent that the solution densities decrease in two ways: (1) by increasing the methane percentage, and (2) by increasing the temperature. Of course, the tendency of higher molar percentages of methane to reduce the mixture density is due to the lower density of methane. As more methane is added to the mixture, the volumetric contribution of methane increases and the volumes of the other, more dense components decrease.

The temperature effect on the solution densities is due to the increased energy of the mixture. Like water, a hydrocarbon solution that absorbs heat experiences some density decrease as the internal energy of the mixture increases.

Standard Volume of Methane Stored

Referring to FIGS. 7 through 9, shown therein are plots of the amount of methane stored in the different solutions compared with the volume of methane in one liter of CNG at 21 MPa and 15° C. It should be noted that there are two parameters of interest in FIGS. 7 through 9: the composition of the solutions and the bubble temperature at which the comparison was made.

The molar composition of the solutions is incremented by percent methane from the base value of 50 percent to the highest value for the particular methane-solvent mixture. The leftmost point in each of the compositional series corresponds to a temperature of −1° C. Moving to the right in the direction of increasing bubble pressure, each line encountered indicates a temperature increase of 6° C. until the upper end of 38° C. is reached.

FIG. 7 is the plot for the methane-butane mixture. The range of the normalized volume of methane per liter of solution spans from 0.52 at about 11 MPa, 38° C. and 50 mole-percent methane to about 0.94 at 15 MPa, −1° C. and 80 percent methane.

The compositional dependence of the volume of methane stored can be seen by examining the curves of constant temperature. These curves are substantially linear, i.e. they have slopes which increase at a constant rate over the range of bubble pressures.

The influence of temperature on the relative volume of methane stored can also be determined from FIGS. 7 through 9. By inspection of the curves of constant composition, the volume of stored methane decreases as the bubble temperature increases.

For 50 to 60 mole percent methane, this effect is substantially linear and roughly constant for all three compositions. However, the higher mole fraction curves begin to depart from linearity and drop faster at the higher temperature ends of the curves. Thus, the relative amount of methane stored becomes very sensitive to small perturbations in the bubble temperature. This behavior is similar to the shapes of the bubble curves depicted in FIGS. 1 through 3.

The significant drop in the volume of methane stored as the pressure and temperature increase delineates a favorable operating region in selecting a system of methane with butane, propane or LPG for use as a motor vehicle fuel. Since it is desirable to increase the stored methane in the liquid solutions, operational conditions should be chosen to coincide with the predictable linear portions of the curves shown in FIGS. 7 through 9.

Referring to FIG. 8, shown therein is the normalized storage of methane for the methane-propane solution. For propane, the minimum value of the normalized storage volume for propane is 0.45 at 10 MPa and 37° C.; the maximum value is about 0.77 at 11 MPa and −1° C.

With reference to FIG. 9, shown therein is the normalized storage of methane for the methane-LPG mixture. For LPG, the minimum stored amount is 0.50 at 11 MPa and 37° C.; the maximum value is 0.87 at 13 MPa and −1° C.

Similarities between the methane-butane plot of FIG. 7 and the methane-propane and methane-LPG graphs of FIGS. 8 and 9, respectively, are readily apparent. The curves of constant temperature and varying mole fraction increase linearly as the mole fraction of methane increases. Further, the slopes of the curves decrease with each temperature increment. However, both the propane and LPG solutions show a faster drop than the butane mixture in the relative volume of methane stored along the constant composition curves.

From FIGS. 7 through 9, one can determine the amount of methane which can be stored in these solutions. For example, FIG. 9 shows that at 16° C. and 12 MPa, a 63–37 mole percent methane-LPG mixture holds about 68 percent of the volume in CNG at 21 MPa and 15° C. This corresponds to a reduction of 42 percent in the pressure which must be maintained. If the temperature of the same composition were lowered to −1° C., the stored amount of methane would increase to 75 percent of CNG (21 MPa and 15° C.). The reduction in pressure would then be nearly 50 percent of that for CNG.

Comparative Energy Densities

In order to compare the energy densities of the methane solutions, the energy densities may be normalized to gasoline having 36,400 MJ/m$^3$ and plotted against the bubble temperature. The pressures are those corresponding to the bubble conditions given in FIGS. 1 through 3 for the methane mixtures of interest.

With reference to FIG. 10, shown therein is the relative energy density of the methane-butane solutions and CNG (21 MPa and 15° C.) versus bubble temperature. At −1° C., the mixture energy densities vary from 65 percent to 45 percent of gasoline (36,400 MJ/m$^3$) for 50 mole percent methane and 80 mole percent methane, respectively. Note that the CNG (21 MPa and 15° C.) provides about one-third the energy density of gasoline (36,400 MJ/m$^3$).

Figure 11:
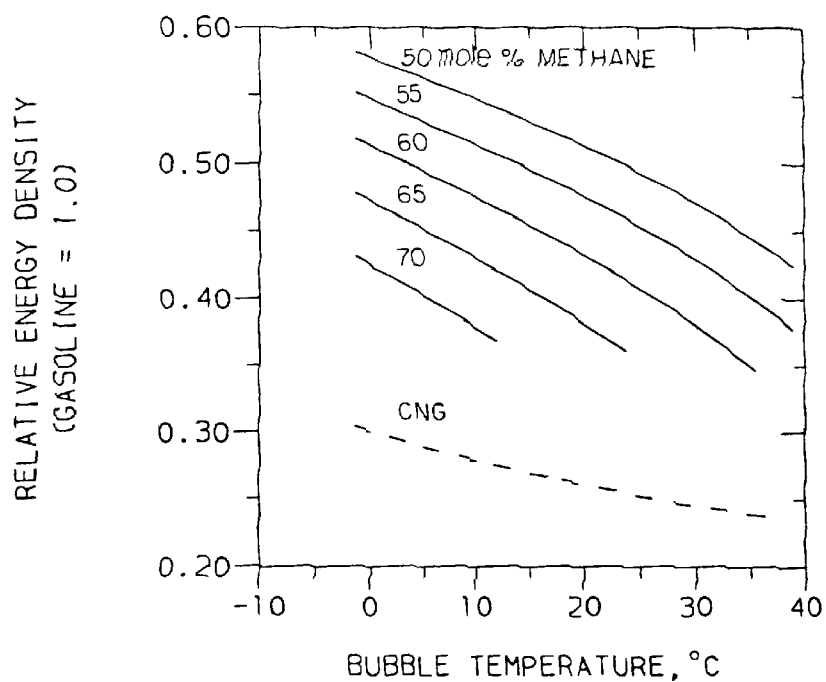
FIG. 11 is a graph of energy density versus bubble temperature for methane in propane solutions between 50 mole percent methane and 70 mole percent methane.

Referring to FIG. 11, shown therein is the relative energy density of the methane-propane solutions versus the bubble temperatures. With similarity to the butane-based solutions, the energy densities of the propane-based solutions decrease with an increase in the temperature and with an increase in the mole fraction of the methane stored.

At −1° C., the 50 mole percent methane-propane solution has 57 percent of the energy density of gasoline (36,400 MJ/m$^3$). Also at −1° C., the 70 mole percent methane mixture with propane has an energy density which is 43 percent of that of the gasoline.

Figure 12:
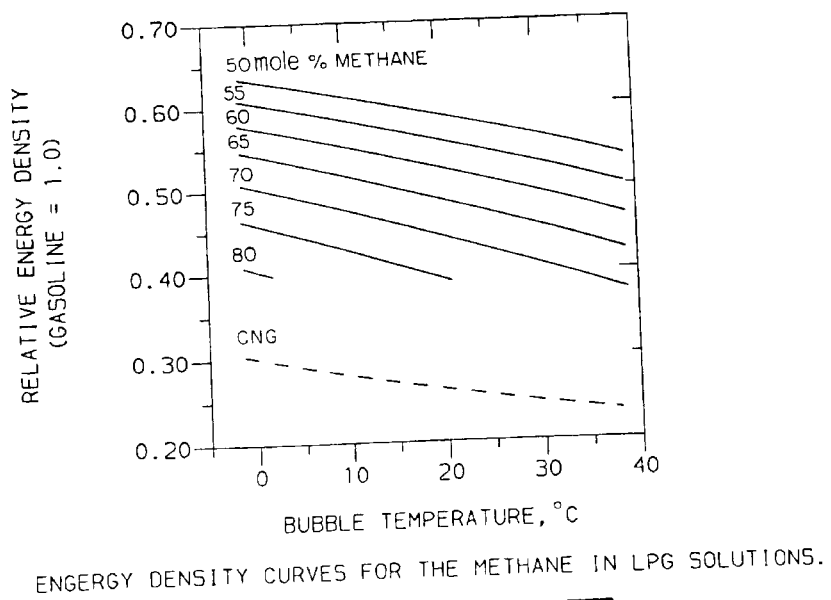
FIG. 12 is a graph of energy density versus bubble temperature for methane in LPG solutions between 50 mole percent methane and 80 mole percent methane.

With reference to FIG. 12, shown therein is the energy density of the methane-LPG solutions relative to gasoline versus the bubble temperatures. As one would expect, the energy densities of the LPG-based solutions decrease with an increase in temperature and with an increase in the mole fraction of the methane stored.

At −1° C., the 50 mole percent methane-LPG solution has 63 percent of the energy density of gasoline (36,400 MJ/m$^3$). Also at −1° C., the 80 mole percent methane mixture with LPG has an energy density which is 41 percent of that in gasoline.

It is interesting to ascertain the energy contribution of methane for the various mole fraction of methane in solution with butane, propane and LPG. This information is presented in the following table.

| Methane Mole Fraction | Butane Methane Energy % Contrib | Propane Methane Energy % Contrib | LPG Methane Energy % Contrib |
|---|---|---|---|
| 50 | 24 | 29 | 25 |
| 55 | 27 | 33 | 29 |
| 60 | 32 | 38 | 34 |
| 65 | 36 | 43 | 38 |
| 70 | 42 | 48 | 44 |
| 75 | 48 | past c.p. | 50 |
| 80 | 55 | past c.p. | 57 |

It can be seen from the above disclosure that storage of methane light hydrocarbon liquids offers a solution to the high pressure stotage requirements of CNG. Over the temperature range of −1° C. to 38° C., the pressures needed for the methane-butane, methane-propane and methane-LPG mixtures were all at least 8 MPa less than that of CNG at 21 MPa and 15° C.

Between −1° C. and 38° C., the energy densities of the methane-butane, methane-propane and methane-LPG mixtures exceed the energy density of CNG. A 50 mole percent methane-butane mixture at −1° C., whit an energy density at 67 percent that of gasoline, appears to offer the greatest energy density of the mixtures analyzed, This amount is more than double the energy density of GNC at 21 MPa, but requires less than half the pressure at about 9 MPa.

Storage in a Motor Vehicle Tank

Figure 13:
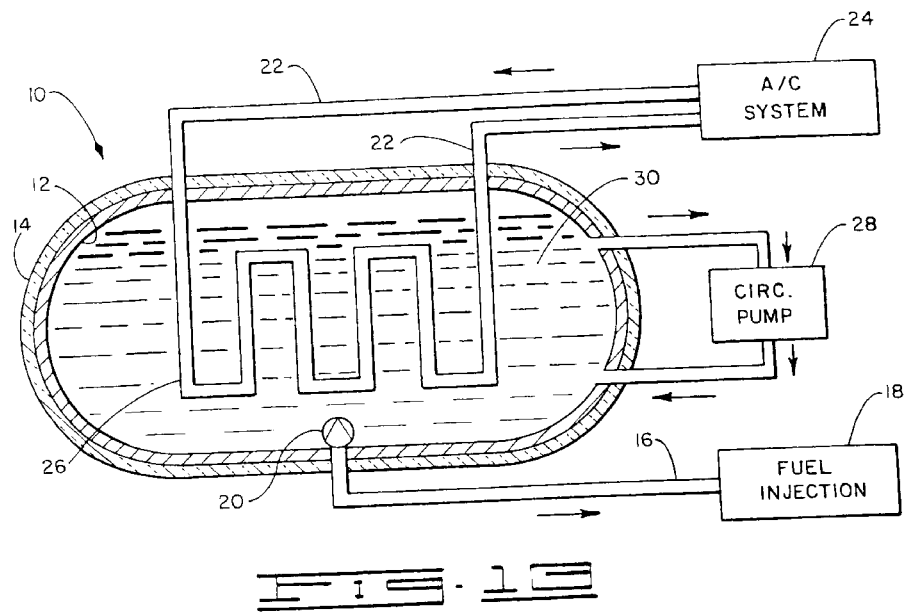
FIG. 13 is a partly diagrammatical, partly sectional view of a vehicle fuel storage system for methane solutions in n-butane, propane or LPG.
Figure 14:
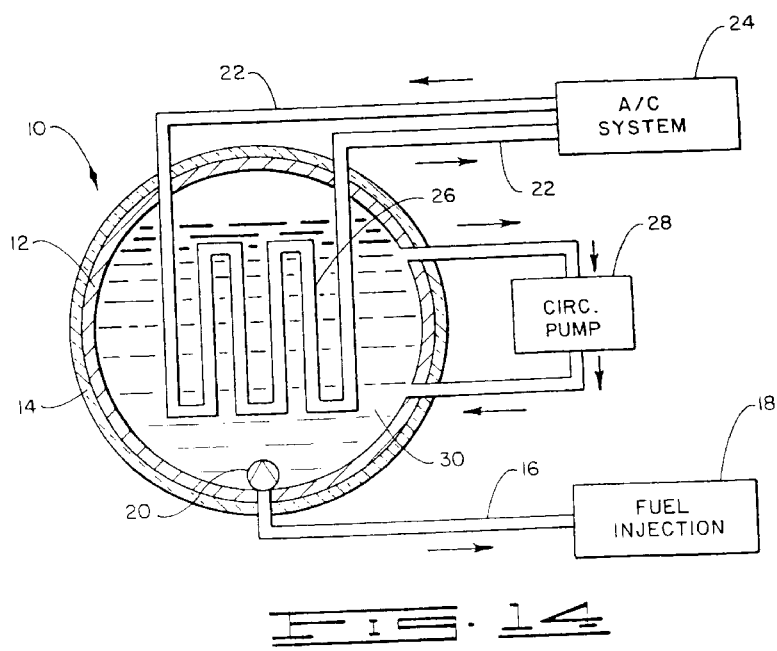
FIG. 14 is a lateral cross-section of the vehicle fuel storage system shown in FIG. 13.

With reference to FIGS. 13 and 14, shown therein and designated by reference numeral 10 is a fuel storage system constructed in accordance with the present invention. The fuel storage system 10 includes a storage tank 12, a layer of insulation 14 surrounding the storage tank 12, a fuel line 16 from the storage tank 12 to the fuel injection system 18 of the vehicle, an expansion valve 20, coolant lines 22 between the storage tank 12 and the AC system 24 of the vehicle, a heat exchanger 26 located within the storage tank 12, and a circulation pump 28.

It should be appreciated that the storage tank 12 has a suitable orifice (not shown) for filling the storage tank 12 with fuel 30 comprising any of the methane and light hydrocarbons solutions, which are disclosed in detail hereinabove. Accordingly, the fuel 30 may be in the approximate range of a 50 mole percent to 80 mole percent methane solution in n-butane, a 50 mole percent to 70 mole percent methane solution in propane, or a 50 mole percent to 80 mole percent methane solution in LPG.

The storage tank 12 may be a 20-gallon CNG-type cylinder with a pressure rating of 21 MPa. The pressure rating of this cylinder is high enough for the working pressures of the methane solutions described hereinabove and high enough to store CNG, if desired. Providing a 21 MPa rated tank allows alternative use of CNG if the methane solutions are not available.

Two vessel materials used in commercially available CNG cylinders are aluminum and a carbon composite. These materials are used singly or in combination for vessel construction. Thus, a range of expected heat transfer may be predicted from the heat transfer associated with these materials.

Further, the insulation 14 may be any type known in the art, such as a fiberglass type similar to that found in home construction. It is reasonable to assume that the insulation 14 is similar to rock wool in its thermal conductivity.

For purposes of evaluation, the storage tank 12 is assumed to be in an isothermal environment at a temperature of 38° C. and out of direct sunlight. The 38° C. temperature is selected arbitrarily as being representative of high temperatures in the United States during summer months. Assuming the storage tank 12 to be out of direct sunlight is necessary to avoid the addition of heat through solar adsorptivity.

The methane solution fuel inside the storage tank 12 is assumed to be at 0° C. This assumption provides the greatest temperature difference between the methane solution fuel and the ambient conditions. Thus, the temperature differential between ambient and the fuel is assumed to be 38° C.

The amount of heat transferred to the fuel 30 from its surroundings may be calculated according to the following equation:

$$q = \frac{\Delta T}{\Sigma R}$$

where q is the amount of heat transferred

ΔT is the difference in ambient and fuel temperatures

R is the resistance to heat transfer.

For purposes of evaluation, the storage tank 12 is assumed to be a hollow cylinder with hemispherical ends. In calculating heat transfer, it is assumed that the heat would be transferred radially across both the body and the ends of the storage tank 12.

The resistances necessary for computing the heat transfer to the fuel 30 are the convective resistances inside and outside the storage tank 12 and the conductive resistance across the insulation 14 and the storage tank wall. The convective resistances may be calculated from the following equation:

$$R_{convective} = \frac{1}{hA_j}$$

where h is the convective heat transfer coefficient

A is the area exposed to convection j denotes the inside or outside area of heat transfer The resistance across the insulation 14 and the storage tank walls was determined by summing the resistances of a hollow sphere and the resistance of a hollow cylinder. The resulting expression is:

$$R_{conductive} = \frac{D_o - D_i}{2\pi k D_o D_i} + \frac{\ln(D_o/D_i)}{2\pi k L}$$

where D is the diameter of the sphere and the cylinder k is the thermal conductivity of the material subscripts o and i represent the outside and the inside of the conducting medium, respectively L is the length of the cylinder.

The dimensions of the storage tank 12 and the pertinent physical properties of the materials are as follows:

| Tank Dimensions | |
|---|---|
| Outer Diameter | 0.35 meters |
| Inner Diameter | 0.31 meters |
| Cylinder Length | 0.85 meters |
| Volume | 0.074 cubic meters |
| Thermal Conductivity, k | |
| Aluminum | 122 kW/mk |
| Composite | 0.36 kW/mk |
| Insulation | 0.04 kW/mk |
| Convective Heat Transfer Coefficients, h | |
| Ambient Air | 0.055 kW/m²k |
| Light Hydrocarbons | 0.284 kW/m²k |

Figure 15:
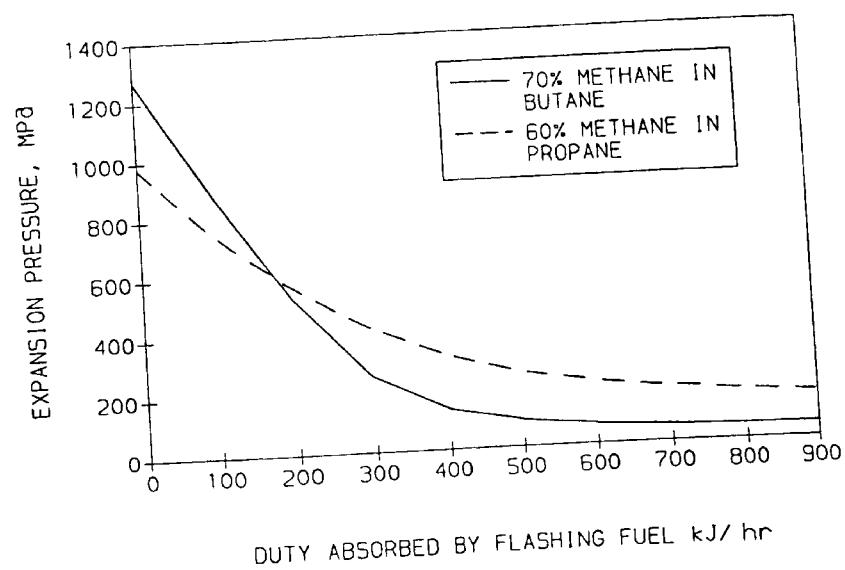
FIG. 15 is a graph of duty absorbed by flashing fuel for a 70 mole percent methane in butane solution and a 60 mole percent methane in propane solution.

These data and the above equations were used to determine the amount of heat leak from ambient air at 32° C. to a liquid fuel at 0° C. as a function of the thickness of the insulation 14. The results of these calculations are illustrated in FIG. 15.

The aluminum tank, having a much higher thermal conductivity than the composite tank, shows greater heat leakage for insulation thickness below one inch. The difference between the two curves quickly decreases with increased insulation thickness.

It should be noted that the curves approach the same value at about one inch of insulation. This convergence indicates that the insulation 14 has become the controlling resistance in the heat transfer to the fuel 30.

Further, it should be observed that the curves become asymptotic to a value of about 950 kJ/hr at one inch of insulation. This characteristic implies that insulation thicker than one inch would not aid greatly in the resistance to heat leakage. Since it is desirable to provide a tank with minimal outer dimensions, the thickness of the insulation 14 should not exceed approximately one inch.

FIG. 15 suggests that the heat leakage to the storage tank 12 with one inch of insulation 14 is about 950 kJ/hr. The addition of this energy to the fuel storage system 10 containing the methane solution at its bubble point would raise the temperature of the fuel 30 and could result in a vapor enrichment of methane and an increase in the system pressure.

Two techniques of heat removal may be utilized, singly or in combination, to control the temperature of the methane solutions in the storage tank 12. The two techniques are: (1) using the vehicle's existing air-conditioning (AC) system; and (2) flashing the liquid fuel in an expansion valve.

Use of Vehicle's AC System

It should be appreciated that many feasible fuel mixtures would require not cooling. Only applications which make use of a sub-ambient storage temperature require consideration of cooling and the consideration of heat leakage.

A typical automobile AC system provides about 19,000 kJ/hr of cooling capacity. For an ambient temperature of 38° C., the cooling load imposed on the typical AC system ranges from about 11,600 kJ/hr to 27,400 kJ/hr. The first value is the load associated with the steady-state operation at a vehicle speed of 30 miles per hour. The second value is the cooling load which occurs in the first ten minutes of operation following a hot soak, i.e. ambient and solar heat saturation.

For the steady-state case, the required removal of 950 kJ/hr from the fuel is only about eight percent of the steady state cooling load. In the hot soak case, the 950 kJ/hr requirement increases the hot soak cooling load by only about three percent. Thus, existing AC systems may be used to provide the required removal of 950 kJ/hr from the methane solution fuels.

As shown in FIGS. 13 and 14, the AC cooling is provided to the methane solution fuel by the coolant lines 22, the heat exchanger 26 and the circulation pump 28. The coolant lines 22 supply AC coolant fluid to the heat exchanger 26.

The circulation pump 28 enhances the performance of the fuel storage system 10 in two ways. First, the circulation pump 28 circulates the methane solution fuel 30 around the heat exchanger 26 to increase the contact of the fuel 30 with the heat exchanger 26. Secondly, the circulation of the fuel 30 by the pump 28 keeps the contents of the storage tank 12 well mixed.

Flash Expansion

Flash expansion involves using the fuel 30 itself to provide cooling to the storage tank 12. Saturated liquid fuel 30 is withdrawn from the storage tank 12 and allowed to expand inside the storage tank 12.

In order to provide the fuel storage system 10 with flash expansion, the expansion valve 20 is located within the storage tank 12. The methane solution fuel 30 is withdrawn from the storage tank 12 through the expansion valve 20. The flashing fuel 30 cools as it expands across the expansion valve 20 and draws heat from the bulk fuel 30 remaining in the storage tank 12. The amount of cooling provided by flash expansion is a function of the mass flow rate of the fuel 30 to the engine of the vehicle and the pressure on the discharge side of the expansion valve 20.

It should be noted that the fuel pressure must be lowered before the fuel is introduced to the engine of the vehicle. Thus, flash expansion not only provides cooling to the bulk fuel 30 in the storage tank 12 but also performs the necessary function of lowering fuel pressure for introduction to the engine.

In order to estimate the amount of cooling which may be provided by flash expansion, the amount of fuel to operate a vehicle must be known. The following table shows several commercially available cargo vans and associated fuel consumption data. Cargo vans are selected as a representative vehicle for a fleet operation.

| Make | Model | Mpg (city) | Mpg (highway) | Engine Size (liters) | Number of Cylinders |
|---|---|---|---|---|---|
| Chevrolet | G1500 | 15 | 19 | 4.3 | 6 |
| | G2500 | 14 | 18 | 5.0 | 8 |
| Dodge | B1500 | 15 | 17 | 3.9 | 6 |
| | B2500 | 13 | 17 | 5.2 | 8 |
| Ford | E150 | 13 | 17 | 4.9 | 6 |
| | Econoline | 14 | 18 | 5.0 | 8 |
| GMC | G1500 | 15 | 19 | 4.3 | 6 |
| | G2500 | 14 | 18 | 5.0 | 8 |
| Average Speed | | 20 mph city | | 48 mph highway | |
| Vehicle Performance | | 6-cyl (city) | 6-cyl (highway) | 8-cyl (city) | 8-cyl (highway) |
| Fuel Consumption (gallons gasoline per hour) | | 1.3 | 2.5 | 1.4 | 2.7 |
| Energy Consumption (MJ per hour) | | 0.18 | 0.34 | 0.19 | 0.35 |

The energy consumption values from the above table may be converted to an equivalent mass of methane solutions from the energy densities, energy fractions and solution densities disclosed hereinabove. This conversion results in a mass flow rate of roughly 3.6 kg per hour for city consumption of a 70 mole percent methane-butane mixture or a 65 mole percent methane-propane solution.

Using the mass flow rate of 3.6 kg per hour, the cooling effect of flash expansion can be approximated. Assuming that the fuel is fed to the expansion valve 20 at 0° C. and the respective saturation pressure, the duty of the expansion valve 20 is illustrated in FIG. 15. The 70 mole percent methane in butane solution is shown as a solid line and the 65 mole percent methane in propane is shown as a dotted line.

FIG. 15 is useful in determining the amount of heat that can be removed from a fuel solution if the outlet pressure of the expansion valve 20 is specified. For the 70 mole percent methane-butane mixture, expansion to 1.4 MPa indicates that about 420 kJ/hr can be removed from the fuel by flash expansion.

The 420 kJ/hr cooling from flash expansion is less than the needed 950 kJ/hr heat leak described hereinabove. Thus, for the 70 mole percent methane-butane fuel solution, heat removal via flash expansion alone is smaller than the heat being leaked into the fuel storage system 10 and heat will accumulate in the storage tank 12. Accordingly, in the case of 70 mole percent methane-butane, supplemental cooling from the AC system of the vehicle is required to prevent heat accumulation.

As illustrated by FIG. 15, flash expansion of the fuel to 1.4 MPa of the 60 mole percent methane in propane solution removes about 950 kJ/hr of heat from bulk fuel 30 in the storage tank 12. Thus, flash expansion of the 60 mole percent methane-propane mixture requires no additional cooling by the AC system while the vehicle is running.

It is apparent from the foregoing estimates that the methane fuel solutions may be maintained at sub-ambient temperatures by flash expansion and the vehicle AC system, particularly in the case of fleet operations. Thus, a solution of methane in light hydrocarbons is a viable vehicular fuel and has advantages in energy density and storage requirements over CNG and LNG.

Changes may be made in the combinations, operations and arrangements of the various parts and elements described herein without departing from the spirit and scope of the invention as defined in the following claims.

What is claimed is:

1. A method for storing a solution of methane and at least one other hydrocarbon, the steps of the method comprising:

mixing gaseous methane with at least one other hydrocarbon to produce a mixture, the mixture comprising a mole percent of methane from about 50 to about 80 percent; and maintaining the mixture of methane and at least one other hydrocarbon as a liquid solution at a temperature of about −1° C. or greater and at a pressure of about 8.0 MPa or greater such that the liquid solution has an energy density of at least about 11,000 MJ/m$^3$.

2. The method of claim 1 further comprising the step of:
circulating the solution of methane and at least one other hydrocarbon within a storage tank.

3. The method of claim 1 wherein the other light hydrocarbon is selected from the group consisting of butane, propane, liquefied petroleum gas, and combinations thereof.

4. A method for storing a solution of methane and at least one other hydrocarbon, the steps of the method comprising:

mixing gaseous methane with at least one other hydrocarbon to produce a mixture, the mixture comprising a mole percent of methane from about 50 to about 80 percent; and maintaining the mixture of methane and at least one other hydrocarbon as a liquid solution at a temperature of about −10° C. or greater and a pressure of about 8.0 MPa or greater such that the liquid solution has an energy density of at least about 11,000 MJ/m$^3$.

5. The method of claim 4 further comprising the step of: circulating the solution of methane and at least one other hydrocarbon within a storage tank.

6. The method of claim 4 wherein the other light hydrocarbon is selected from the group consisting of butane, propane, liquefied petroleum gas, and combinations thereof.

7. A method for storing a solution of methane and at least one other hydrocarbon, the steps of the method comprising:
mixing gaseous methane with at least one other hydrocarbon to produce a mixture, the mixture comprising a mole percent of methane from about 50 to about 80 percent; and
maintaining the mixture of methane and at least one other hydrocarbon as a liquid solution at ambient temperature and at a pressure of about 8.0 MPa or greater such that the liquid solution has an energy density of at least about 11,000 MJ/m$^3$.

8. The method of claim 7 further comprising the step of:

circulating the solution of methane and at least one other hydrocarbon within a storage tank.

9. The method of claim 7 wherein the other light hydrocarbon is selected from the group consisting of butane, propane, liquefied petroleum gas, and combinations thereof.

* * * * *

UNITED STATES PATENT AND TRADEMARK OFFICE
CERTIFICATE OF CORRECTION

PATENT NO. : 6,111,154 Page 1 of 1
DATED : August 29, 2000
INVENTOR(S) : Richard G. Mallinson, Kenneth E. Starling and Jeffrey H. Harwell It is certified that error appears in the above-identified patent and that said Letters Patent is hereby corrected as shown below:

Drawings,
FIGs. 11 and 12, delete the word "ENGERGY" and substitute therefor -- ENERGY --.

Column 6,
Line 19, after "incremented by" insert -- 5 --.

Column 7,
Line 45, delete "5".

Column 8,
Line 27, delete "whit" and substitute therefor -- with --.
Line 30, delete "GNC" and substitute therefor -- CNG --.

Signed and Sealed this

Fifth Day of March, 2002

Attest:

Attesting Officer

JAMES E. ROGAN
*Director of the United States Patent and Trademark Office*